(12) United States Patent
Shariati

(10) Patent No.: US 10,034,734 B2
(45) Date of Patent: Jul. 31, 2018

(54) HYSTEROPEXY MESH APPARATUSES AND METHODS

(71) Applicant: Coloplast A/S, Humlebaek (DK)

(72) Inventor: Amir Shariati, Parkland, FL (US)

(73) Assignee: Coloplast A/S, Humlebaek (DK)

( * ) Notice: Subject to any disclaimer, the term of this patent is extended or adjusted under 35 U.S.C. 154(b) by 85 days.

(21) Appl. No.: 15/218,084

(22) Filed: Jul. 25, 2016

(65) Prior Publication Data

US 2016/0331501 A1 Nov. 17, 2016

Related U.S. Application Data

(63) Continuation of application No. 14/449,459, filed on Aug. 1, 2014, now Pat. No. 9,480,546.

(60) Provisional application No. 61/862,386, filed on Aug. 5, 2013.

(51) Int. Cl.
*A61F 2/00* (2006.01)
*A61B 17/42* (2006.01)

(52) U.S. Cl.
CPC ........ *A61F 2/0045* (2013.01); *A61B 17/4241* (2013.01); *A61F 2/0063* (2013.01); *A61F 2/0095* (2013.01); *A61F 2002/0072* (2013.01); *A61F 2230/0019* (2013.01); *A61F 2230/0043* (2013.01)

(58) Field of Classification Search
CPC .................. A61F 2/0063; A61F 2/0045; A61F 2230/0019; A61F 2230/0043; A61F 2002/0072; A61F 2/0095; A61B 17/4241
See application file for complete search history.

(56) References Cited

U.S. PATENT DOCUMENTS

2008/0021265 A1* 1/2008 Garbin ............. A61B 17/06109
600/30
2010/0264954 A1* 10/2010 Drost .................. H01L 23/3171
326/30

FOREIGN PATENT DOCUMENTS

WO 2014008130 A1 1/2014

\* cited by examiner

*Primary Examiner* — Christine H Matthews
*Assistant Examiner* — Joshua D Lannu
(74) *Attorney, Agent, or Firm* — Coloplast Corp., Coloplast A/S; Nick Baumann

(57) ABSTRACT

A hysteropexy apparatus includes a hysteropexy mesh and a package containing the hysteropexy mesh. The hysteropexy mesh includes an anterior vaginal portion that is substantially rectangular in shape, a right broad ligament portion that is substantially L-shaped, a left broad ligament portion that is substantially L-shaped, a sacral portion that is substantially rectangular in shape, and a posterior vaginal portion that is substantially rectangular in shape. The anterior vaginal portion is folded on a longitudinal midline. The sacral portion is folded onto the posterior vaginal portion.

18 Claims, 5 Drawing Sheets

HYSTEROPEXY MESH APPARATUSES AND METHODS

FIELD OF THE INVENTION

The invention relates generally to apparatuses and methods for performing hysteropexy.

BACKGROUND OF THE INVENTION

Uterine prolapse occurs when pelvic floor muscles and ligaments stretch and weaken, providing inadequate support for the uterus. The uterus then descends into or protrudes from the vagina. Uterine prolapse can happen to women of any age, but it often affects postmenopausal women who've had one or more vaginal deliveries. Damage to supportive tissues during pregnancy and childbirth, effects of gravity, loss of estrogen, and repeated straining over the years all can weaken the pelvic floor and lead to uterine prolapse.

At the present time, sacral colpopexy is the gold standard procedure for post-hysterectomy patients who have vaginal vault prolapse. Patients who still have their uterus and are undergoing sacral colpopexy are having a total hysterectomy or a supracervical hysterectomy at the same time. This can lead to mesh erosion. The only reason that most hysterectomies are performed is because the appropriate mesh that can provide anterior, posterior, and apical uterine support is not available. Hysteropexy is the surgical fixation of a displaced uterus. The hysteropexies that are performed at the present time are either supporting the uterus by placing the mesh anteriorly or posteriorly.

BRIEF SUMMARY OF THE INVENTION

The present invention provides embodiments of apparatuses and methods configured for use in hysteropexy and methods of using the same.

In one embodiment, a hysteropexy is presented comprising a hysteropexy mesh comprising: an anterior vaginal portion, substantially rectangular in shape, having a major dimension of about 10 cm and a minor dimension of about 4.0 cm; a right broad ligament portion, substantially L-shaped, extending from one long edge of the anterior vaginal portion and having a thickness dimension about 1.2 cm and a major dimension of about 3.5 cm; a left broad ligament portion, substantially L-shaped, extending from the other long edge of the anterior vaginal portion and having a thickness dimension about 1.2 cm and a major dimension of about 3.5 cm; a sacral portion, substantially rectangular in shape, having a major dimension of about 8.0 cm and a minor dimension of about 4.0 cm; and a posterior vaginal portion, substantially rectangular in shape, having a major dimension of about 15 cm and a minor dimension of about 4.0 cm; where the left broad ligament portion extends between and connects the anterior vaginal portion and the posterior vaginal portion.

In another embodiment the hysteropexy mesh comprises one of polypropylene, polyester, polyethylene, silicone, a urethane, a polyurethane, copolymers, or block copolymers thereof.

In another embodiment a method of treating hysteropexy is provided comprising: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesicouterine fascia incision and bladder flap; dissect vesicovaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina; pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix; attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

In another embodiment the hysteropexy procedure is performed robotically, laparoscopically, or in open surgery through a laparotomy incision.

In yet another embodiment a medical device kit is provided comprising the hysteropexy mesh of the current disclosure and instructions for implantation.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Embodiments and methods for using a hysteropexy mesh configured to be implanted in the pelvic region of a patient are discussed below.

Figure 1:
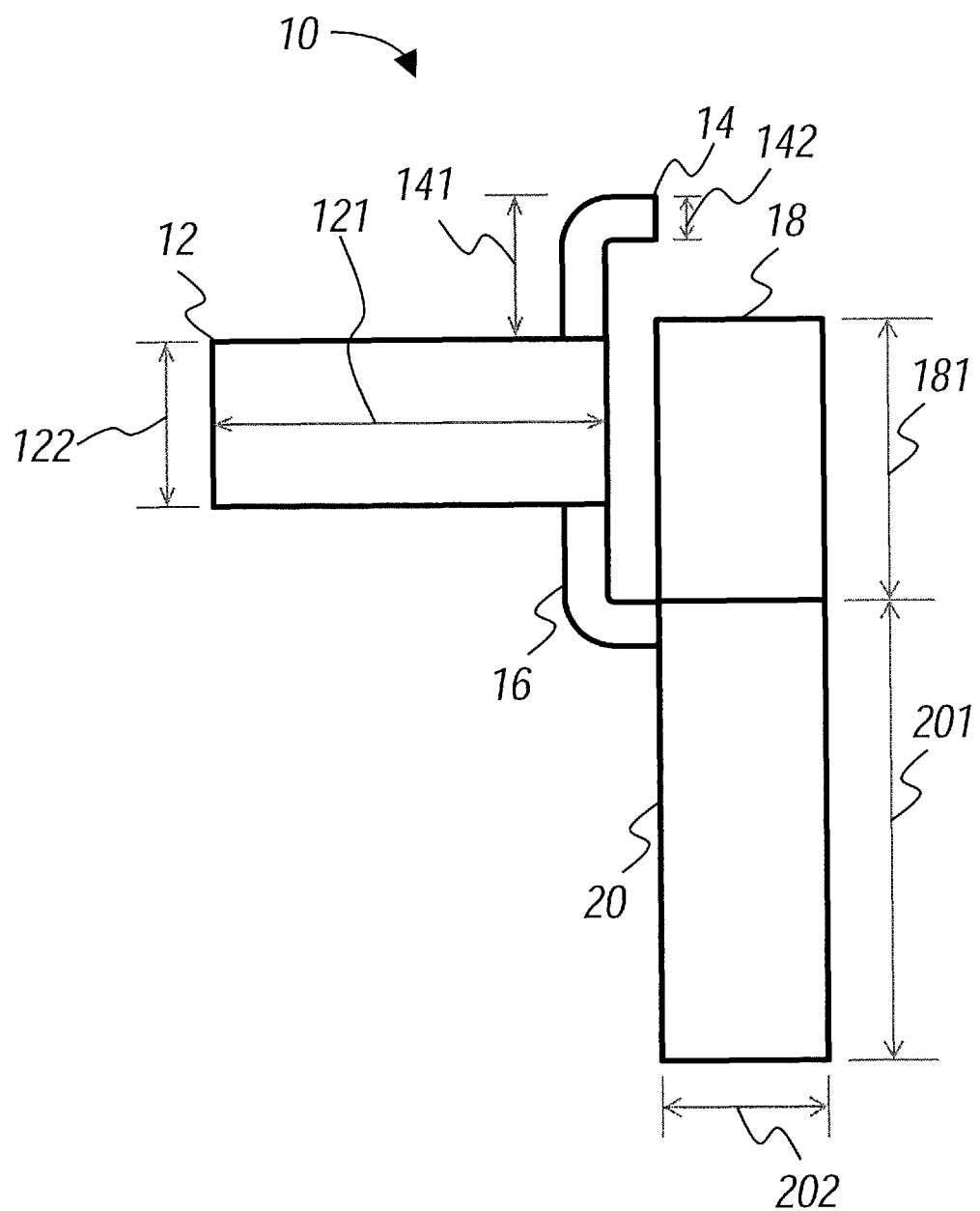
FIG. 1 is a plan view of an embodiment of a hysteropexy mesh comprising an anterior vaginal portion, a right broad ligament portion, a left broad ligament portion, a sacral portion, and a posterior vaginal portion.

A plan view of an embodiment of a hysteropexy mesh 10 is shown in FIG. 1. Mesh 10 comprises an anterior vaginal portion 12, a right broad ligament portion 14, a left broad ligament portion 16, a sacral portion 18, and a posterior vaginal portion 20.

In the illustrated embodiment, mesh 10 is an integral mesh, and each of the above-identified portions 12-20 are regions of the whole. In such embodiments, mesh 10 may be cut, stamped, or otherwise machined from a single sheet of mesh.

In other embodiments, the portions may be separate or separable. For example, in certain embodiments, anterior vaginal portion 12, right broad ligament portion 14, and left broad ligament portion 16 may comprise one integral mesh, sacral portion 18 may comprise a second integral mesh, and posterior vaginal portion 20 may comprise a third integral mesh, and these may be coupled to each other, such as with a suture or an ultrasonic weld.

In the illustrated embodiment, anterior vaginal portion 12 is substantially rectangular in shape with a major dimension 121 of about 10 cm and a minor dimension 122 of about 4.0 cm.

Right broad ligament portion 14 extends from the long edge of anterior vaginal portion 12, such that an edge of right broad ligament portion 14 is in common (i.e., substantially aligned) with a short edge of anterior vaginal portion 12.

Left broad ligament portion 16 extends from the other long edge of anterior vaginal portion 12, such that an edge of left broad ligament portion 16 is in common (i.e., substantially aligned) with the same short edge of anterior vaginal portion 12 and the edge of right broad ligament portion 14.

Right and left broad ligament portions 14 and 16 are substantially L-shaped, and may be rounded as shown in FIG. 1. Each of the broad ligament portions has a thickness dimension 142 of about 1.2 cm and a major dimension 141 of about 3.5 cm.

Left broad ligament portion 16 is between anterior vaginal portion 12 and posterior vaginal portion 20. Posterior vaginal portion 20 is substantially rectangular in shape and has a major dimension 201 of about 15 cm and a minor dimension 202 of about 4.0 cm. The edge of left broad ligament portion 16 that is in common with the edge of anterior vaginal portion 12 and the edge of right broad ligament portion 14 is also in common with a short edge of posterior vaginal portion 20.

Sacral portion 18 is substantially rectangular in shape and has a major dimension 181 of about 8 cm and a minor dimension 202 of about 4.0 cm.

Figure 2:
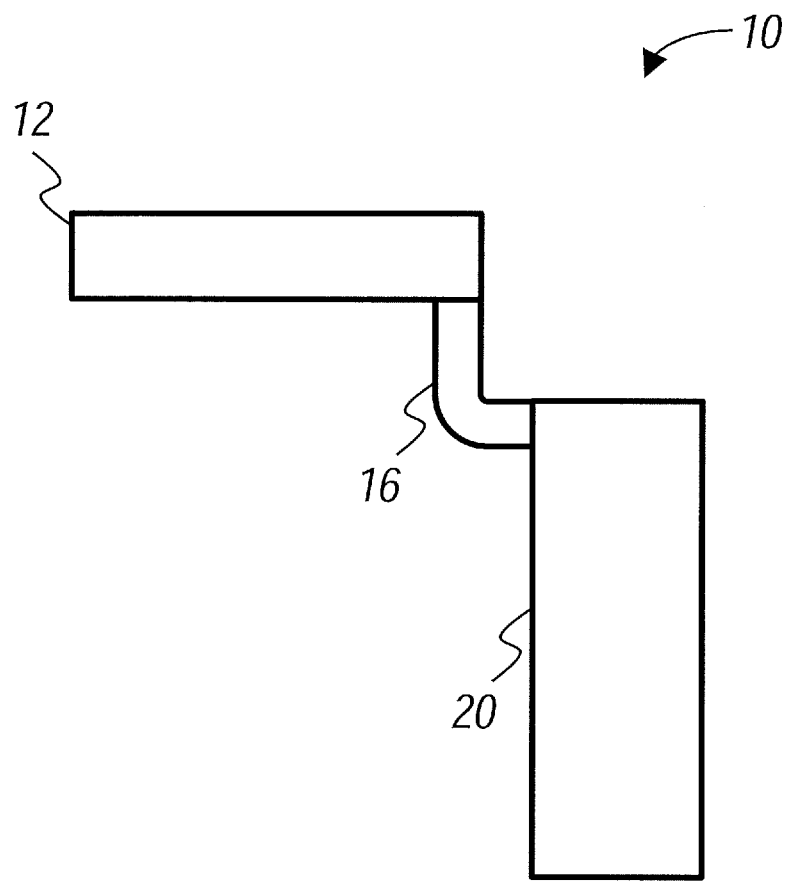
FIG. 2 is a plan view of an embodiment of a hysteropexy mesh with anterior vaginal portion folded along its longitudinal midline.

As shown in FIG. 2, mesh 10 is configured to be folded substantially along the longitudinal midline of anterior vaginal portion 12 and is further configured to be folded between sacral portion 18 and posterior vaginal portion 20. In certain embodiments, mesh 10 is packaged as depicted in FIG. 2, such that mesh 10 is folded substantially along the longitudinal midline of anterior vaginal portion 12 and between sacral portion 18 and posterior vaginal portion 20. In such embodiments, mesh 10 may be removed from the packaging, passed through the left side broad ligament incision, then unfolded to be attached to the anterior vaginal wall.

Figure 3:
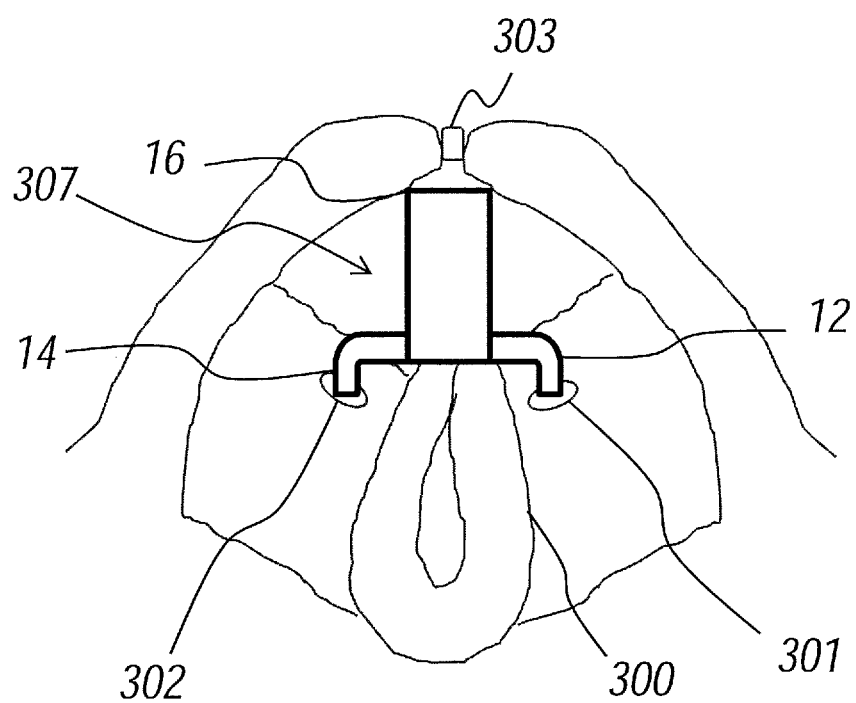
FIG. 3 is an anterior view of an embodiment of a hysteropexy mesh implanted in the pelvic region showing the uterus, the pubic bone, and the anterior vagina.
Figure 4:
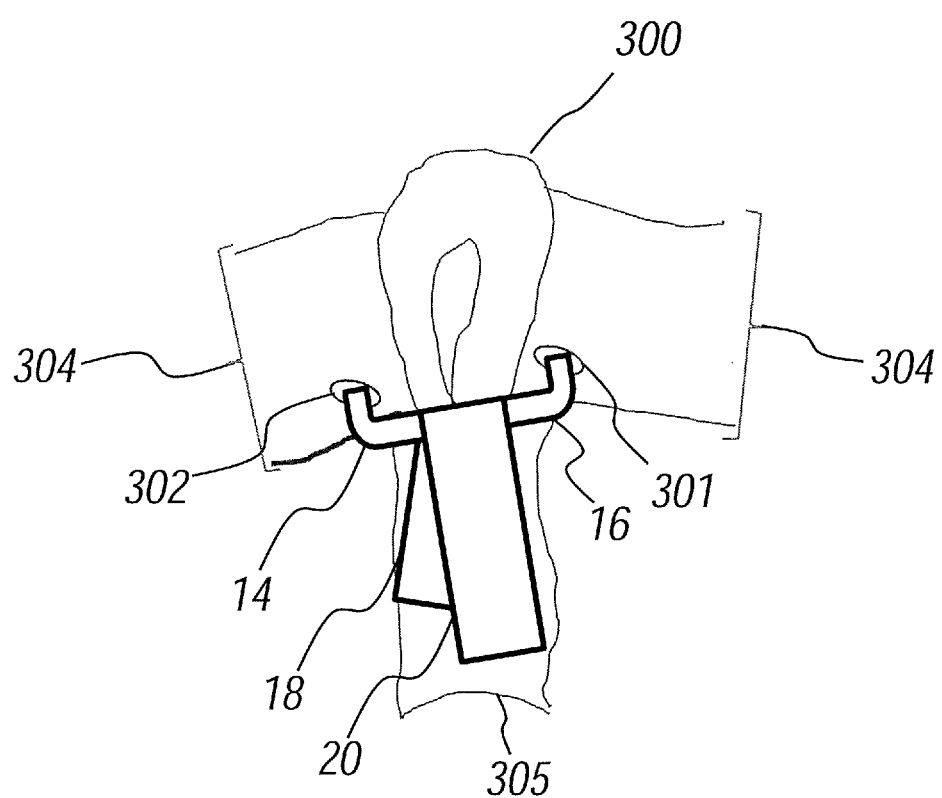
FIG. 4 is a posterior view of an embodiment of a hysteropexy mesh implanted in the pelvic region showing the uterus, the broad ligament, and a portion of the sacrum.
Figure 5:
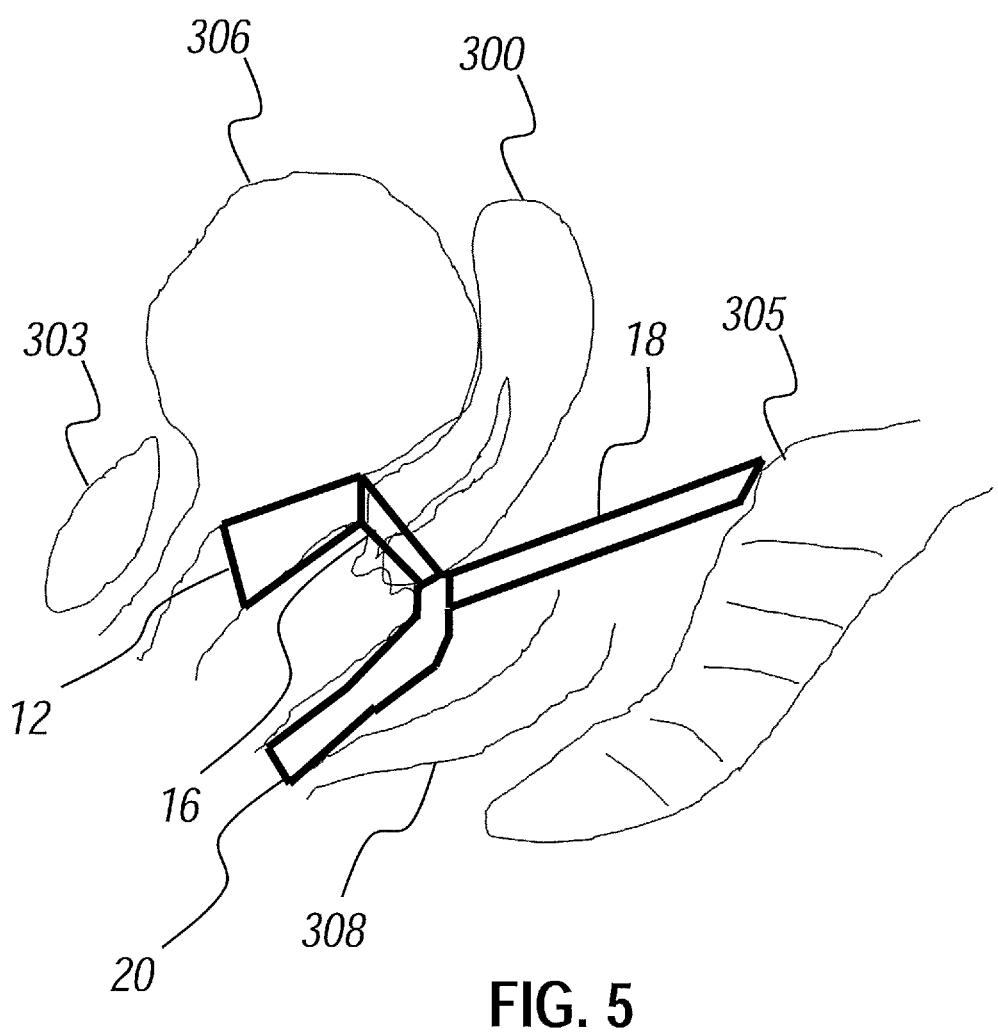
FIG. 5 is a lateral view of an embodiment of a hysteropexy mesh implanted in the pelvic region showing the pubic bone, the bladder, the uterus, the rectum, and the sacrum.

FIGS. 3-5 are anterior, posterior, and lateral illustrations, respectively, of mesh 10 implanted into the pelvic region of a patient. FIG. 3 is an anterior view of mesh 10 implanted in the pelvic region showing the uterus 300, the pubic bone 303, and the anterior vagina 307. FIG. 4 is a posterior view of mesh 10 implanted in the pelvic region showing uterus 300, the broad ligament 304, and a portion of the sacrum 305. FIG. 5 is a lateral view of mesh 10 implanted in the pelvic region showing pubic bone 303, bladder 306, uterus 300, rectum 308, and sacrum 305. These figures may be reference to better understand the steps of embodiments of the method discussed below.

In one embodiment, the mesh 10 is a knitted monofilament polypropylene mesh having a mass per area between approximately 15-35 g/m$^2$ with a pore size between approximately 500-1500 μm and a thickness of approximately 260 μm. This mesh is thin and light weight (i.e., the basis weight is less than approximately 35 g/m$^2$) to provide a thin and comfortable mesh that is less likely to erode tissue that contacts the mesh and less likely to be sensed through the tissue layers by the patient. Other suitable materials for the support include fabrics formed from polyester, polyethylene, silicone, urethanes, polyurethanes, copolymers, or block copolymers of these or suitably similar polymeric materials. Suitable such knitted monofilament polypropylene mesh is available from Coloplast Corp., Minneapolis, Minn. Other suitable woven polypropylene mesh material is available from, for example, HemiaMesh, Chivasso, Italy.

Embodiments of the disclosed method may be performed robotically, laparoscopically, or in open surgery through a laparotomy incision.

In embodiments where the method is performed robotically, a uterine manipulator may be placed vaginally to allow for manipulation of uterus 300 for the anterior and posterior dissection of the vaginal walls and attachment of the mesh. Then a robotic tenaculum may be used to grab the fundus of the uterus to manipulate the uterus for the anterior and posterior dissection of the vaginal walls and attachment of the mesh. A tenaculum can then be used through an accessory port to be placed on the fundus of the uterus to manipulate the uterus for the anterior and posterior dissection of the vaginal walls and attachment of the mesh.

In embodiments where the procedure is being performed laparoscopically, the tenaculum may be used to be placed on the fundus of uterus 300 to manipulate uterus 300 for the anterior and posterior dissection of the vaginal walls and attachment of the mesh or a uterine manipulator may be placed vaginally to allow for manipulation of uterus 300 for the anterior and posterior dissection of the vaginal walls and attachment of the mesh.

In embodiments where the procedure is being performed open through a laparotomy incision a uterine manipulator may be placed vaginally to allow for manipulation of uterus 300 for the anterior and posterior dissection of the vaginal walls and attachment of the mesh.

In the disclosed embodiments, the other steps of the method may be performed as follows.

Uterus 300 is elevated so the posterior vagina is visualized. An incision is made in the peritoneum just above the rectum 308. Dissection is then performed bluntly and sharply in the rectovaginal space to separate rectum 308 from the posterior aspect of the vagina until the perineal body is reached and the levator muscles are exposed.

After that, the peritoneum overlying the sacral promontory is tented up and entered sharply with scissors. The peritoneal dissection is then carried inferiorly to meet the dissection posteriorly in the cul de sac below. The anterior longitudinal ligament as well as the presacral vessels on the sacral promontory are identified and cleared off.

Uterus 300 is then pulled dorsally and apically so that the anterior aspect of uterus 300 and the vagina are visualized. An incision is made in the vesicouterine fascia and the bladder flap is created sharply. The dissection is performed bluntly and sharply in the vesicovaginal space to separate the bladder from the anterior aspect of the vagina. This is done until the level of the trigone is reached.

Two one-centimeter incisions 301, 302 are made with the use of scissors and/or cautery in the broad ligament on each side near the cervix.

Then, posterior vaginal portion 20 of mesh 10 is attached to the posterior aspect of the vagina, such as with interrupted sutures.

The folded anterior vaginal portion 12 and the right and left broad ligament arms 14, 16 are then passed through incision 301 in the broad ligament on the left.

Anterior vaginal portion 12 is then unfolded and attached to the anterior aspect of the vagina using interrupted sutures.

Right broad ligament portion 14 is then passed through incision 302 in the broad ligament on the right. Uterus 300 is then lifted again, such as with a tenaculum or a manipulator and right broad ligament portion 14 of mesh 10 is attached to posterior vaginal portion 20 of mesh 10 and the posterior aspect of the cervix.

Sacral portion 18 of mesh 10 is than attached to the anterior longitudinal ligament at the level of the S1 vertebrae, such as with two interrupted sutures in tension free fashion.

To minimize exposure of the mesh to intraperitoneal organs, posterior vaginal portion 20 of mesh 10 and the peritoneal incision made on the sacrum are than closed using absorbable suture. Anterior vaginal portion 12 of mesh 10 is then covered with the bladder peritoneum using another absorbable suture. Any remaining incisions are closed and the surgery is complete.

In the specification and in the claims, the terms "including" and "comprising" are open-ended terms and should be interpreted to mean "including, but not limited to . . . ." These terms encompass the more restrictive terms "consisting essentially of" 180 and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 to 6 provide for various aspects of the present invention.

In one embodiment, in a first paragraph (1), the present invention provides a hysteropexy mesh comprising: an anterior vaginal portion, substantially rectangular in shape, having a major dimension of about 10 cm and a minor dimension of about 4.0 cm; a right broad ligament portion, substantially L-shaped, extending from one long edge of the anterior vaginal portion and having a thickness dimension about 1.2 cm and a major dimension of about 3.5 cm; a left broad ligament portion, substantially L-shaped, extending from the other long edge of the anterior vaginal portion and having a thickness dimension about 1.2 cm and a major dimension of about 3.5 cm; a sacral portion, substantially rectangular in shape, having a major dimension of about 8.0 cm and a minor dimension of about 4.0 cm; and a posterior vaginal portion, substantially rectangular in shape, having a major dimension of about 15 cm and a minor dimension of about 4.0 cm; where the left broad ligament portion extends between and connects the anterior vaginal portion and the posterior vaginal portion.

(2) The hysteropexy mesh of claim 1, wherein the mesh comprises one of polypropylene, polyester, polyethylene, silicone, a urethane, a polyurethane, copolymers, or block copolymers thereof.

(3) A method of treating hysteropexy comprising: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesicouterine fascia incision and bladder flap; dissect vesicovaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina; pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix; attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

(4) The method of paragraph (3), wherein the procedure is performed robotically, laparoscopically, or in open surgery through a laparotomy incision.

(5) A medical device kit comprising: the hysteropexy mesh of paragraph (1); and instructions for the implantation of the medical device.

(6) The medical device kit of paragraph (5), wherein the instructions comprise: create a peritoneal incision just above the rectum; separate rectum from the posterior aspect of the vagina by dissection until the perineal body is reached and the levator muscles are exposed; penetrate peritoneum overlying the sacral promontory and inferiorly dissected to meet posterior dissection from cul de sac; identify and clear off anterior longitudinal ligament and presacral vessels on the sacral promontory; manipulate uterus to create vesicouterine fascia incision and bladder flap; dissect vesicovaginal space to separate the bladder from the anterior aspect of the vagina until the level of the trigone is reached; create broad ligament incisions on each side near the cervix; insert hysteropexy mesh and attach by suture the posterior vaginal portion of the mesh to the posterior aspect of the vagina;

pass folded anterior vaginal portion and right and left broad ligament arms through incision in the broad ligament on the left; unfold anterior vaginal portion and attach by suture to the anterior aspect of the vagina; pass right broad ligament portion through incision in the broad ligament on the right; manipulator uterus and attach right broad ligament portion of mesh to posterior vaginal portion of mesh and the posterior aspect of the cervix; attach sacral portion of mesh to the anterior longitudinal ligament at the level of the S1 vertebrae by suture in a tension free fashion; close peritoneal incision made on the sacrum by suture and cover with the bladder peritoneum using another suture; and close any remaining incisions to complete procedure.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A hysteropexy apparatus comprising:
   a hysteropexy mesh including:
   an anterior vaginal portion that is substantially rectangular in shape, wherein the anterior vaginal portion is folded along a longitudinal midline of the anterior vaginal portion,
   a right broad ligament portion that is substantially L-shaped, the right broad ligament portion extending from a major side of the anterior vaginal portion forming a substantially perpendicular angle in between,
   a left broad ligament portion that is substantially L-shaped, the left broad ligament portion extending from another major side of the anterior vaginal portion forming a substantially perpendicular angle in between,
   a sacral portion that is substantially rectangular in shape, and
   a posterior vaginal portion that is substantially rectangular in shape, wherein a minor side of the sacral portion is connected to a minor side of the posterior vaginal portion, the sacral portion is folded onto the posterior vaginal portion along the connected minor side of the sacral portion; and
   a package containing the hysteropexy mesh;
   wherein the anterior vaginal portion, the right broad ligament portion, and the left broad ligament portion form a first integral mesh, the sacral portion forms a second integral mesh, and the posterior vaginal portion forms a third integral mesh, the first, second, and third integral meshes are configured to be separable from each other.

2. The hysteropexy apparatus of claim 1, wherein the left broad ligament portion extends between and connects the anterior vaginal portion and the posterior vaginal portion.

3. The hysteropexy apparatus of claim 1, wherein the hysteropexy mesh is made with at least one selected from the following: polypropylene, polyester, polyethylene, silicone, urethane, polyurethane, copolymers, and block copolymers.

4. The hysteropexy apparatus of claim 1, wherein the right broad ligament portion includes rounded corners.

5. The hysteropexy apparatus of claim 1, wherein the left broad ligament portion includes rounded corners.

6. The hysteropexy apparatus of claim 1, wherein the package further includes surgical instructions for implanting the hysteropexy mesh.

7. A hysteropexy mesh comprising:
   an anterior vaginal portion that is substantially rectangular in shape;
   a right broad ligament portion that is substantially L-shaped, the right broad ligament portion extending from a major side of the anterior vaginal portion forming a substantially perpendicular angle in between;
   a left broad ligament portion that is substantially L-shaped, the left broad ligament portion extending from another major side of the anterior vaginal portion forming a substantially perpendicular angle in between;
   a sacral portion that is substantially rectangular in shape; and
   a posterior vaginal portion that is substantially rectangular in shape;
   wherein a minor side of the sacral portion is connected to a minor side of the posterior vaginal portion;
   wherein the anterior vaginal portion, the right broad ligament portion, and the left broad ligament portion form a first integral mesh, the sacral portion forms a second integral mesh, and the posterior vaginal portion forms a third integral mesh, the first, second, and third integral meshes are configured to be separable from each other.

8. The hysteropexy mesh of claim 7, wherein the left broad ligament portion extends between and connects the anterior vaginal portion and the posterior vaginal portion.

9. The hysteropexy mesh of claim 7, wherein the right broad ligament portion extends between and connects the anterior vaginal portion and the posterior vaginal portion.

10. The hysteropexy mesh of claim 7, comprising at least one material selected from the following: polypropylene, polyester, polyethylene, silicone, urethane, polyurethane, copolymers, and block copolymers.

11. The hysteropexy mesh of claim 7, wherein the right broad ligament portion includes rounded corners.

12. The hysteropexy mesh of claim 7, wherein the left broad ligament portion includes rounded corners.

13. A method comprising the steps:
    disposing an anterior vaginal portion of a hysteropexy mesh between a bladder and a vagina, the anterior vaginal portion of the hysteropexy mesh being substantially rectangular;
    penetrating a right broad ligament portion of the hysteropexy mesh through a broad ligament, the right broad ligament portion of the hysteropexy mesh being L-shaped;
    penetrating a left broad ligament portion of the hysteropexy mesh through the broad ligament, the left broad ligament portion of the hysteropexy mesh being L-shaped;
    extending a sacral portion of the hysteropexy mesh between a uterus and a sacrum, the sacral portion of the hysteropexy mesh being substantially rectangular; and
    disposing a posterior vaginal portion of the hysteropexy mesh between the vagina and a rectum, the posterior vaginal portion of the hysteropexy mesh being substantially rectangular;
    wherein the left and the right broad ligament portions connect the anterior vaginal portion, the posterior vaginal portion, and the sacral portion of the hysteropexy mesh.

14. The method of claim 13, further comprising forming a first incision through the broad ligament at a right side of the uterus and penetrating the right broad ligament portion of the hysteropexy mesh through the first incision.

15. The method of claim 14, further comprising forming a second incision through the broad ligament at a left side of the uterus and penetrating the left broad ligament portion of the hysteropexy mesh through the second incision.

16. The method of claim 13, wherein
a minor side of the sacral portion of the hysteropexy mesh is connected to the right and the left broad ligament portions of the hysteropexy mesh; and
another minor side of the sacral portion of the hysteropexy mesh is connected the sacrum.

17. The method of claim 13, wherein
a minor side of the posterior vaginal portion of the hysteropexy mesh is connected to the right and the left broad ligament portions of the hysteropexy mesh; and
another minor side of the posterior vaginal portion of the hysteropexy mesh is connected to a tissue disposed between the vagina and the rectum.

18. The method of claim 13, wherein
a minor side of the anterior vaginal portion of the hysteropexy mesh is connected to the right and the left broad ligament portions of the hysteropexy mesh; and
another minor side of the anterior vaginal portion of the hysteropexy mesh is connected to a tissue disposed between the vagina and the bladder.

\* \* \* \* \*